United States Patent [19]

Duvos et al.

[11] Patent Number: 5,783,558
[45] Date of Patent: Jul. 21, 1998

[54] PARATHORMONE FRAGMENTS, THEIR PREPARATION AND MEDICAMENTS CONTAINING THESE

[75] Inventors: Christian Duvos, Stade; Hubert Mayer, Wolfenbüttel; Bernd Mueller-Beckmann, Grünstadt; Klaus Strein, Hemsbach; Edgar Wingender, Wolfenbüttel, all of Germany

[73] Assignee: Boehringer Mannheim GmbH, Mannheim, Germany

[21] Appl. No.: 256,363

[22] PCT Filed: Feb. 4, 1993

[86] PCT No.: PCT/EP93/00259

§ 371 Date: Jul. 20, 1994

§ 102(e) Date: Jul. 20, 1994

[87] PCT Pub. No.: WO93/15109

PCT Pub. Date: Aug. 5, 1993

[30] Foreign Application Priority Data

Feb. 4, 1992 [DE] Germany .......... 42 03 040.4

[51] Int. Cl.$^6$ .......... A61K 38/29; C07K 14/635
[52] U.S. Cl. .......... 514/12; 530/324
[58] Field of Search .......... 530/324, 399; 514/12

[56] References Cited

U.S. PATENT DOCUMENTS

| | | | |
|---|---|---|---|
| 4,423,037 | 12/1983 | Rosenblatt et al. | 424/177 |
| 4,833,125 | 5/1989 | Neer et al. | 514/12 |
| 5,252,705 | 10/1993 | Kammera et al. | 530/324 |
| 5,358,934 | 10/1994 | Borovsky et al. | 514/15 |
| 5,393,869 | 2/1995 | Nakagawa et al. | 530/324 |
| 5,434,246 | 7/1995 | Fukuda et al. | 514/12 |
| 5,457,092 | 10/1995 | Schluter et al. | 514/12 |
| 5,578,567 | 11/1996 | Cardinaux et al. | 514/12 |

FOREIGN PATENT DOCUMENTS 9106564  5/1991  WIPO.

OTHER PUBLICATIONS

Kikuchi et al, *Endocrinology*, vol. 128, No. 3, pp. 1229–1237 (1991).

Somjen et al. Stimulation by defined parathyroid hormone fragments . . . Biochem. J. 1990, vol. 272, pp. 781–785.

Copy of specification of U.S. application serial No. 70/225, 344 (Jul. 28, 1988).

*Primary Examiner*—Jeffrey E. Russel
*Attorney, Agent, or Firm*—Nikaido Marmelstein Murray & Oram LLP

[57] ABSTRACT

The invention concerns parathormone (PTH) fragments including the amino acid range of the natural parathormone of +3 to +35 and their physiologically compatible derivatives, a process for the preparation of the fragments according to the solid phase and liquid phase synthesis from partly blocked amino acids contained in the fragments which are coupled with one another in the sequence which corresponds to the amino acid sequence in the fragments to be prepared and medicaments containing at least one of the fragments, especially with calcium-regulating action in the body.

10 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ser  Glu  Ile  Gln  Leu  Met  His  Asn  Leu  Gly  Lys  His  Leu  Asn  Ser
 1              5                        10                       15

Met  Glu  Arg  Val  Glu  Trp  Leu  Arg  Lys  Lys  Leu  Gln  Asp  Val  His
                20                       25                       30
```

Asn Phe Val ( 2 ) INFORMATION FOR SEQ ID NO:2:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Ser Glu Ile Gln Leu Met His Asn Leu Gly Lys His Leu Asn Ser
1               5                       10                      15

Met Glu Arg Val Glu Trp Leu Arg Lys Lys Leu Gln Asp Val His
                20                      25                      30

Asn Phe Val Ala ( 2 ) INFORMATION FOR SEQ ID NO:3:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Ser Val Ser Glu Ile Gln Leu Met His Asn Leu Gly Lys His Leu
1               5                       10                      15

Asn Ser Met Glu Arg Val Glu Trp Leu Arg Lys Lys Leu Gln Asp
                20                      25                      30

Val His Asn Phe Val
                35

( 2 ) INFORMATION FOR SEQ ID NO:4:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Ser Val Ser Glu Ile Gln Leu Met His Asn Leu Gly Lys His Leu
1               5                       10                      15

Asn Ser Met Glu Arg Val Glu Trp Leu Arg Lys Lys Leu Gln Asp
                20                      25                      30

Val His Asn Phe Val Ala
                35

PARATHORMONE FRAGMENTS, THEIR PREPARATION AND MEDICAMENTS CONTAINING THESE

The invention concerns new parathyroid hormone (PTH) fragments, as well as their pharmacologically compatible derivatives, the preparation of these fragments and of their derivatives by chemical ways and medicaments containing these.

Parathyroid hormone (PTH), a hormone of the adrenal glands, is an important regulator inter alia for the maintenance of the calcium level in the body. PTH can stimulate the bone formation or bone resorption. It thereby acts as regulatory hormone on a series of enzymes, inter alia ornithine decarboxylase and adenylate cyclase (cAMP synthesis). In the case of calcium deficiency, PTH mobilises calcium from the bones, reduces the calcium excretion of the kidneys and simultaneously improves the resorption of calcium from the intestine by means of an increased synthesis of 1,25-$(OH)_2D_3$. Due to the action on these target organs, a normalisation of the calcium level is achieved. On the other hand, in the case of increased calcium level, the incorporation of calcium into the bones is stimulated. Furthermore, PTH shows a mitogenic effect, especially a stimulation of osteoblasts and chondrocytes.

Furthermore, from DE-OS 37 25 319, it is known that the above-mentioned effect is brought about by a special region of the PTH and that it is possible to achieve the same action by administration of PTH fragments which correspond to this region (see also Sömjen et al., Biochem. J. (1990) 272, 781–785; Shurtz-Swirski et al., Acts Endocrinol. (1990) 122, 217–226 and Potts et al, Advances in Protein chemistry (1982) 35, 323–396). From this literature, it is also to be found how such PTH fragments can be prepared and varied, whereby not only a cleavage of the naturally-occurring PTH but also chemically synthetic or gene-technological processes are possible. A chemically synthetic process for the preparation of hPTH (1-37) is described in the International Application WO 91/06564. However, this known solid phase and liquid phase synthesis has the disadvantage that the yields in the case of the preparation are relatively low.

PTH fragments are especially interesting for the treatment of osteoporosis. However, it has been found that the fragments are of differing effectiveness and that in some cases, e.g. in the case of the use of hPTH(1-34), the action is positive in the case of some patients but in others an impairment of the calcium retention occurred and the total bone mass diminished during the treatment.

Therefore, it is the task of the invention to make available new PTH fragments which have an improved therapeutic action, especially in the case of the regulation of the calcium level in the body and in the case of the incorporation of calcium into the bones. Furthermore, these fragments are to be preparable with a relatively small expense in good yield.

This task is solved with PTH fragments which include the amino acid sequences of bPHT(3-35), pPTH(3-35) or hPTH(3-35), whereby the C-terminal end of these sequences can be extended by one amino acid or the N-terminal end by one or two amino acids. In particular, in the meaning of the invention, there come into question the PTH fragments (1-35) and (1-36). In the sequence protocol, there are contained the amino acid sequences of the following fragments:
SEQ ID No. 1; core fragment hPTH(3-35)
SEQ ID No. 2: hPTH(3-36)
SEQ ID No. 3: hPTH(1-35)
SEQ ID No. 4: hPTH(1-36)

Furthermore, the subject of the invention is a process for the preparation of these fragments in that one prepares the said fragments or part fragments thereof by means of liquid phase synthesis from protected amino acids which are coupled with one another in the sequence so that the desired amino acid sequence of the particular fragment results. The subject of the invention are also medicaments which contain a PTH fragment according to the invention as active material, besides usual adjuvant and additive materials.

The amino acid sequences of hPTH, bPTH and pPTH (h=human, b=bovine, p=porcine) are known from Potts et al., Adv. in Protein Chem. (1982), 323–396; e.g. hPTH(1-34).

The PTH fragments according to the invention with the amino acid region of PTH(3-35) which, starting from the amino acid position +3, can be extended on the N-terminus by one or two amino acids, are especially those fragments which possess the amino acids D- or L-Val in position +2. Fragments which are extended by two amino acids on the N-terminus possess in position +2 the amino acid D- or L-Val and in position +1 the amino acid D- or L-Ser.

Fragments which are extended on the C-terminus, starting from the amino acid position +35 (Val), by one amino acid represent especially those fragments which have the amino acid D- or L-Ala in position +36.

Preferably, the fragments PTH(1-35) come into question with the amino acid sequence Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-Val SEQ ID No.3 and PTH(1-36) with the amino acid sequence Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe-Val-Ala SEQ ID No.4.

The carboxyl group of the amino acid on the C-terminal end can be present in free form or in the form of a physiologically compatible alkali metal or alkaline earth metal salt, such as e.g. the sodium, potassium or calcium salt. The carboxyl group can also be amidated with primary or secondary amines, such as e.g. ammonia, $C_1$–$C_6$-alkylamine or di-$C_1$–$C_6$-alkylamines, especially methylamine or dimethylamine, i.e. —$CONR^1R^2$ with $R^1$=hydrogen, $C_1$–$C_6$-alkyl and $R^2$=hydrogen, $C_1$–$C_6$-alkyl, whereby the alkyl group can signify, for example, methyl, ethyl, n-propyl, i-propyl, butyl etc.

In this meaning, there preferably come into question the fragments PTH(2-35), PTH(2-35)-Z, PTH(1-35), PTH(1-35)-Z, PTH(2-36), PTH(2-36)-Z, PTH(1-36) or PTH(1-36)-Z, especially the corresponding hPTH fragments, whereby Z signifies the above-given amidated carboxyl group —$CONR^1R^2$. $R^1$ especially signifies a hydrogen atom and $R^2$ a methyl, ethyl or isopropyl group.

The PTH fragments according to the invention possess advantageous therapeutic properties. In particular, with them there can be regulated not only the calcium level in the body but also the incorporation of calcium into the bones can be objectively promoted for which reason they can favourably influence the course of osteoporosis or bring this to a stop. This action is surprising because these PTH fragments, unlike the known fragments hPTH(1-37) or hPTH(1-34), do not belong to the biologically-active hPTH fragments which result by primary cleavage of the hPTH(1-84) in the human body. As further advantage of the PTH fragments according to the invention is to be added that they can be prepared in better yield than the fragments with longer amino acid sequence.

In comparison with the known fragments hPTH(1-n) with n=34, 37 or 38, the PTH fragments according to the invention possess a surprisingly higher effectiveness in various test systems so that they are better suitable for a therapeutic use than the previously known fragments. The advantages of the new fragments are especially the following: stronger mitogeneity and DNA synthesis capacity; lower catabolic, calcium-mobilising action; lower cAMP activation; increase of the calcium retention and strengthened calcium incorporation into the bones. In all, these effects bring about a clearly superior anabolic action of the new PTH fragments compared with the previously known PTH fragments.

The solid phase and liquid phase synthesis is a conventional process also already employed for the synthesis of hPTH fragments (see WO 91/06564). However, it is disadvantageous in the case of this process that many impurities are also produced which not only make the pure preparation difficult but also reduce the yields.

In order to optimise the process for the preparation of a particular product with regard to the purity of the crude product and the yield, it is necessary to adapt the process parameters and the materials used, for example the materials for the blocking of the groups which are not to react or the reagents which split off blocking materials, to the product to be prepared, to the intermediate products to be prepared or starting materials. Having regard to the interdependence of the many process parameters, this adaptation is not simple. In the case of the preparation of the PTH modifications according to the invention, it is advantageous when the "reagent K" used for the separating off of the synthetised peptide from the solid phase and of the side group blockings contains dithiothreitol (DTT) as component instead of ethanedithiol.

It has been shown that the filter process known from the article "Simultaneous Multiple Peptide Synthesis under Continuous Flow Conditions on Cellulose Paper Discs as Segmental Solid Supports" by R. Frank et al., published in Tetrahedron, Vol. 44, No. 19, pp. 603–604 (1988), is, in principle, also suitable for the preparation of, for example, hPTH(1-35) and hPTH(1-36) but PTH fragments which go beyond the number 36 can only produced with this method with clearly reduced yield in pure form—presumably because of the formation of large amounts of impurities.

Medicaments which contain fragments according to the invention individually or together as active material, besides usual adjuvant and additive materials, were preferably administered parenterally. The medicament has a calcium-regulating action and thereby promotes in advantageous manner the incorporation of calcium into the bones. It is advantageous for the use of the medicament when it contains the active material in amounts of 300 micrograms to 30 milligrams per dose unit. In particular, a good action is then achieved when the dose unit of fragment according to the invention corresponds to 100 to 1000 units or to an effective concentration of $10^{-8}$–$10^{-7}$ M/l of body fluids The PTH fragments according to the invention are preferably stored as sterile lyophilisate and are mixed with a suitable isotonic solution before the administration. In this form, the fragments can then be injected, infused or possibly also absorbed through the mucous membranes. As solvents, there can be used the usual isotonic, aqueous systems suitable for the injection or infusion. Physiological common salt solution or solutions possibly made isotonic by buffers are, in this case, preferred.

The daily dosage to be administered depends upon the indication. In the case of the therapy of osteoporosis by i.v./i.m. injection, it lies in the range of 100 to 1200 units (μg)/day, in the case of daily subcutaneous injection preferably at 300–2400 units (μg)/day. The determination of the biological activity is based on measurements against international reference preparations for HPTH fragments in a conventional biological test process for hPTH fragments.

The PTH fragments according to the invention can be prepared according to the filter synthesis process or the convention protocol via a commercial synthesiser.

EXAMPLE 1

Chemical synthesis of hPTH(1-35) and hPTH(1-36)

In the case of the preparation according to the process of the invention (chemical synthesis), a Milligen 9050 peptide synthesiser is employed in advantageous manner. Pentafluorophenyl esters of the amino acids were used in combination with hydroxybenzotriazole (HOBt) for the prevention of racemisations during the coupling reaction. N-alpha-amino functions were protected by the fluorenyl-methoxycarbonyl group (Fmoc). Amino acid side chains were protected by t-Boc(histidine and lysine), t-But (aspartic acid, glutamic acid and serine) and Pmc (2,2,5,7,8-pentamethylchromane-6-sulphonyl)(arginine). As resins, there were preferably used:- Fmoc-Val-NovaSyn-PA 500 (Novabiochem), substitution degree 0.37 mMol/g for hPTH(1-35) and Fmoc-Ala-NovaSyn-PA 500 (Novabiochem), substitution degree 0.35 mMol/g for hPTH(1-36).The splitting off of the peptides from the resin and the splitting off of protective groups was carried out with a mixture of trifluoroscetic acid (TFA), phenol, water, thioanisole and dithiothreitol (DTT). A mixture of 82.5% TFA, 5% phenol, 5% water, 5% thioanisole and 2.5% DTT and modified reagent K (see King et al., Int. J. Peptide Protein Res. 36, 255–266, 1990) is thereby preferably allowed to act in each case for about two hours. The Fmoc group was thereby split off by means of a solution of piperidine in dimethylformamide (DMF). The solution was preferably 20%. The crude peptides were precipitated with t-butyl methyl ether, dissolved in water/acetonitrile—preferably 9:1—preferably pre-purified over C-18 cartridges (J. T. Baker Chemical Co.) and lyophilised.

In the case of preparation under the preferred conditions, the yield amounted to 71% for hPTH(1-35) and 67% for hPTH(1-36). The crude peptides were purified by preparative HPLC—preferably on reversed phase-C4 (RP-4) material with a water-acetonitrile gradient. The yield amounts to 10–15%, referred to the crude peptides.

EXAMPLE 2

Preparation of hPTH(1-35) and hPTH(1-36) according to the filter method.

The synthesis in the case of use of the filter method took place according to the Fmoc/t-butyl (tBu) method with use of the 1-hydroxybenzotriazole (HOBt)/ diisopropylcarbodiimide (DICD) coupling. As special side chain protective groups, there were used Pmc for Arg, trimethoxybenzyl (Tmob) for Asn and Gln and butoxycarbonyl (Boc) for His.

In the case of the preparation of the PTH fragments according to the filter method, for each sequence there were used two filters with a loading of, in each case, 5 μmol C-terminal amino acid derivative. Each sequence was thus prepared on the scale of 10 μMol.

Before commencement of the synthesis, the cellulose filters were first prepared for the reception of the amino acids. For this purpose, the filter paper was caused to swell by gentle acid treatment, e.g. with a 10% solution of TFA in dichloromethane and subsequently reacted with a "coupling-on compound". A coupling of the benzyl ester type was preferred in order to anchor the first amino acid to the carrier. Especially favourable as "coupling-on compound"—also with regard to the later separating off—was a p-alkoxybenzyl derivative with the formula I,

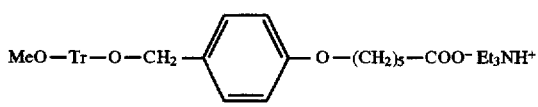

which has a 4-methoxytrityl ether group as protecting group, which can easily be split off with dichloro-acetic acid in dichloromethane. The compound can be prepared by selective tritylation of 4-hydroxyphenol with 4-methoxytrityl chloride. The methoxytrityl group is needed as protective group in the esterification of the cellulose hydroxyl groups with the alkoxy-benzyl derivative.

The attachment of the first Fmoc-amino acid was carried out as in the case of other carriers substituted with benzyl alcohol in that a threefold excess was brought to reaction with the reacted substrate via the filter loading of preactivated amino acid derivatives with use of dimethyleminopyridine (DMAP) as catalyst. The preactivation was achieved in that the Fmoc-protected amino acid derivative was reacted with 1-hydroxybenzotriazole (HOBt) and diisopropylcarbodiimide (DICD) to give the HOBT ester. The amino acid derivatives were preferably reacted in DMF with 1.5 equivalents of HOBt and 1.2 equivalents of DICD for 45 minutes. The preactivated aminoacid derivatives were applied in situ to the filter papers where the amino acid was coupled on with the acid end. For the preparation of the coupling-on of the second and of the further amino acids, the Fmoc group of the last coupled-on amino acid was split off with a—preferably—20% solution of piperidine in DMF. Subsequently, there then followed the coupling on of the next Fmoc-protected amino acid, the amide formation was tested by the bromophenol blue indicator (see V. Krchnak et al. Collect. Czech, Chem. Commun. 53, 2542 (1988) and was complete after 0.5 to 2 hours.

After the conclusion of the peptide synthesis, there followed the TFA-promoted separating off of the peptide from the alkoxybenzyl alcohol derivative. The t-But groups for the side group protection were thereby also separated off. For this purpose, there was preferably used a TFA/anisole/dichloromethane mixture, the optimum composition of which was 55 volume % TFA, 5 volume % anisol and 40 volume % dichloromethane.

The split off crude peptides were extracted with ether and subsequently lyophilised. The yield amounted to 43 mg for hPTH(1-35) and 34 mg for hPTH(1-36). The so-prepared crude peptide was purified by preparative RP chromatography—preferably—on C4 silica gel.

EXAMPLE 3

Determination of the action of various PTH fragments on the Ca retention in the case of rats.

The measurement of the Ca balance in growing rats is a suitable model to test in vivo the effectiveness of a systemically administered substance on the bone metabolism. In the case of the Ca balance, the Ca flows in and out of the body are measured and the Ca retention (balance) calculated therefrom. It is thereby taken into account that the bones store about 99% of the body calcium, whereas the plasma calcium level remains constant. The amount of calcium retained in the body from the nutrition can, therefore, be regarded as proportional to the growth in the bone mass.

As experimental animals for the investigations, there served male CD rats which, at the beginning of the experiment, were 10 weeks old and weighed 250–300 g. The experimental animals were kept individually in commercially-available metabolic cages. An automatic separation of faeces and urine took place in the metabolic cages. Both fractions were collected quantitatively in collection containers and could be analyzed separately from one another.

As feed there served a standard diet for rats of meal-like consistency which was pasted with aqua dist. in the ratio of 1:1. The daily provided amount of feed was so adapted to the feed requirement of the animals in the sense of a so-called "group feedings" that they were completely eaten by all animals. The daily food ration amounted to 20 g (wet feed). Aqua dist. was offerred to the animals ad libitum.

All test substances were injected daily subcutaneously in equimolar doses (corresponding to 40 g hPTH(1-34)×kg$^{-1}$× day$^{-1}$), over 10 days. Of this, the first 7 days served for the adaptation of the animals, whereas the measurement of the Ca balance took place during the last 3 days.

The Ca intake was calculated via the amount of feed taken up and the experimentally determined Ca content of the feed. For this purpose, from the feed batch of each day, an aliquot was dried to constant weight and the water content determined from the comparison of wet and dry weight. Subsequently, 2×500 mg of the dried feed was digested with a laboratory microwave apparatus in conc. acids as follows: To 500 mg of dried feed were successively pipetted 3 ml HNO$_3$ (conc.), 1 ml HCl (conc.) and 1 ml H$_2$O$_2$ (30%). After the subsidence of the spontaneous oxidation reaction (foaming up), there followed the digestion pressure-controlled in closed digestion containers of Teflon PFA. The pressure/time steps were thereby successively following passed through: 40 psi (276 kpa), 5 min; 80 psi (552 kPa), 5 min; 150 psi (1.035 kPa); 10 min. To the cooled digest were then again added 2 ml H$_2$O$_2$ (30%) in order to test the completeness of the digestion reaction (no more foaming up).The digest was made up with a 1% lanthanum nitrate solution (v/v in 0.3% HCl) ad 100 ml. For the measurement of the Ca content on a flame atom absorption spectrometer (AAS), the samples were again dilute 1:100 with 1% lanthanum nitrate solution. The Ca intake was then calculated from the taken-up amount of feed and the measured water and Ca content.

The Ca loss via the faeces was then determined analogously to the Ca intake: Determination of the water content, acidic digestion in the microwave apparatus under the same conditions and subsequent measurement of the Ca content on the AAS.

In the collection container for the urine was placed 2 ml 10% HCl in order to prevent a precipitation of urate. After the end of the experiment, the urine volume was determined by weighing and subsequently an aliquot thereof diluted with 1% lanthanum nitrate solution (v/v in 0.3% HCl) in the ratio of 1:100. The determination of the Ca content of the samples took place on the AAS.

Results:

The results are given in the following Table:

TABLE 1

| substance | Ca retention (mg per day) | | |
|---|---|---|---|
| | average value | +/− SD | % increase |
| control | 49.5 | 5.32 | 0 |
| hPTH(1-34) | 91.8 | 10.25 | 85 |
| hPTH(1-35) | 108.6 | 9.21 | 119 |
| hPTH(1-36) | 110.5 | 11.44 | 123 |
| hPTH(1-37) | 96.0 | 7.69 | 94 |
| hPTH(1-38) | 91.8 | 9.68 | 85 |

Evaluation:

Surprisingly, it was found that the parathormone fragments with a chain length of 35 or 36 amino acids— corresponding to the peptide sequences PTH(1-35) and PTH(1-36)—lead to a higher Ca retention and a clearly more marked incorporation rate of calcium in the bones than the peptides hPTH(1-n) with n=34, 37, 38 known from the state of the art. An increased Ca retention was also found when the peptides were N-terminally shortened by one amino acid.

EXAMPLE 4

Mitogeneity on sterna organ cultures

The mitogeneity of the new fragments was tested in organ cultures from sterna and it was ascertained that this activity was more strongly marked than in the case of the known fragments hPTH(1-34) and hPTH(1-38)(cf. Tab. 2).

TABLE 2

| Mitogeneity on sterna organ cultures | | |
|---|---|---|
| | n | E/C +/− SEM |
| control | 4 | 1.00 +/− 0.13 |
| hPTH (1-34) | 4 | 2.94 +/− 0.38 |
| hPTH (1-35) | 4 | 3.13 +/− 0.57 |
| hPTH (1-36 | 4 | 3.37 +/− 0.58 |
| hPTH (1-38) | 4 | 2.96 +/− 0.30 |

EXAMPLE 5

DNA synthesis capacity on ROS 17/2.8 cells

The DNA synthesis capacity was measured on ROS 17/2.8 cells. Surprisingly, the synthesis capacity was more strongly increased by the fragment PTH(1-35) than by other fragments (cf. Tab. 3). Tab. 3: DNA synthesis hPTH(1-X), 100 nM, ROS/2.8 cells

TABLE 3

| DNA synthesis hPTH (1-X), 100 nM, ROS/2.8 cells | | | |
|---|---|---|---|
| X | n | [³H]-thymidine incorporation (cpm) | E/C |
| basal value | 4 | 663 ± 49 | 1.0 ± 0.07 |
| 34 | 5 | 2,148 ± 289 | 3.2 ± 0.44 |
| 35 | 6 | 2,686 ± 282 | 4.1 ± 0.43 |
| 36 | 6 | 2,136 ± 246 | 3.2 ± 0.37 |
| 37 | 6 | 2,021 ± 251 | 3.1 ± 0.38 |

The induction by hPTH (1-35), hPTH (1-36) and hPTH (1-37) with <p 0.001 increased with regard to the basal rate, 1-34 with p < 0.01.

EXAMPLE 6 cAMP stimulation

In organ cultures from sterna, as well as on membrane fractions from pigs' kidneys was measured the induction of the cAMP formation by various PTH peptides. Surprisingly, this activity decreased for the fragments PTH(1-35) and PTH(1-36) compared with PTH(1-34)(cf. Tab. 4 and Tab. 5). This is of importance since the catabolic, i.e. calcium-mobilising properties of PTH are, as is known, involved with an increase of the cAMP (Schlüter et al. (1989), J. Biol. Chem. 264, 19:11087–11092; Lowik et al., (1988), Calcif Tissue Int. 43:7–18). These findings are plausible and, therefore, support the above-mentioned findings which show an increase of the anabolic properties of the peptide in the case of a chain length between 35 and 36 amino acids.

TABLE 4

| cAMP stimulation on sterna organ cultures 100 nm inductor | | |
|---|---|---|
| | n | pMol cAMP |
| control | 4 | 4.7 |
| 1-34 | 4 | 25.8 |
| 1-35 | 4 | 18.2 |
| 1-36 | 4 | 17.6 |

TABLE 5

| cAMP stimulation on porcine kidney membrane | |
|---|---|
| | pMol cAMP/mg protein ± SEM |
| basal synthesis | 20.6 ± 1.2 |
| hPTH (1-34) | 86.6 ± 1.0 |
| hPTH (1-35) | 82.4 ± 0.4 |
| hPTH (1-36) | 44.6 ± 1.8 | with in each case n = 3 and p < 0.001

EXAMPLE 7

DNA synthesis capacity on PTH-(3-X) fragments

An increased DNA synthesis capacity on UMR 106 cells was also observed with fragments, the N-terminus of which was shortened by two amino acids. An action maximum was again present when the chain length lay between 34 and 36 amino acids (cf. Tab. 6). This finding is surprising since it is known that a deletion of the amino acids +1 or +1 and +2 leads to the loss of the cAMP induction, combined with the loss of the calcium-mobilising properties of the PTH. An anabolic (mitogenic) activity of N-terminal shortened PTH fragments has hitherto not been described.

TABLE 6a

| DNA synthesis PTH (3-X), 100 nM, UMR 106 cells | | | |
|---|---|---|---|
| X | n | [³H]-thymidine incorporation (cpm) | E/C |
| basal value | 5 | 925 ± 48 | 1.0 ± 0.04 |
| 34 | 5 | 1,748 ± 150 | 1.9 ± 0.12 |
| 35 | 4 | 2,591 ± 115 | 2.8 ± 0.1 |
| 36 | 5 | 2,230 ± 172 | 2.4 ± 0.14 |
| 37 | 5 | 2,161 ± 74 | 2.3 ± 0.06 |
| 38 | 5 | 1,905 ± 159 | 2.1 ± 0.13 |

All inductions with p < 0.001 increased in comparison with the basal rate

TABLE 6b

| DNA synthesis PTH (3-X), 300 nM, UMR 106 cells | | | |
|---|---|---|---|
| X | n | [³H]-thymidine incorporation | E/C |
| basal value | 4 | 972 ± 32 | 1.0 ± 0.03 |
| 34 | 5 | 3,516 ± 297 | 3.6 ± 0.31 |
| 35 | 5 | 4,158 ± 213 | 4.3 ± 0.22 |
| 36 | 5 | 4,950 ± 401 | 5.1 ± 0.41 |
| 37 | 5 | 3,962 ± 268 | 4.1 ± 0.28 |
| 38 | 5 | 3,701 ± 414 | 3.8 ± 0.43 |

All inductions with p < 0.001 increased in comparison with the basal rate

EXAMPLE 8

Synthesis of PTH(1-35), PTH(1-35)-Z with Z=NH 2, NH($C_{2-5}$)

The synthesis of the peptides was carried out according to the solid phase method, namely, with the following protective groups:

Protective groups:

α-amino groups: Fmoc

His (Im): trityl

Asp (βCOOH): OtBu

Glu (γCOOH): OtBu

Lys (ε-$NH_2$): BOC

Ser (OH): tBu

Arg (Gus): Pmc

The amide functions of Asn and Gln remain unprotected.

Loading of the resin 25 g p-benzyloxybenzyl alcohol resin ("alkoxy-resin", Novabiochem) were loaded with 13.5 g Fmoc-ValOH and 8.5 g DCC (41 mmol) in DMF/dichloromethane (3:7) with addition of 0.5 g (3.9 mMol) 4-dimethyl-aminopyridine.

After blocking of the excess free OH groups on the resin by means of benzoyl chloride/pyridine and washing with DMF, isopropanol and diisopropyl ether (2 cycles) and drying, one obtained 32 g of Fmoc-Val-resin.

After splitting off of the protective group with 20% piperidine in DMF, there was given a loading of 0.66 mMol/g (indirect determination by UV measurement at 300 nm in the wash liquid via the cleavage products /J. Maienhofer, C. D. Chang Int. J. Pept. Prot. Res 11, 246 (1978)7.

Washing and synthesis cycles:

1. DMF 2×5 min.
2. Fmoc cleavage 20% piperidine in DMF 10 min.
3. Fmoc cleavage 20% piperidine in DMF 20 min.
4. washing DMF 4×5 min.
5. washing 2-propanol 2×5 min.
6. washing DMF 2×5 min.
7. coupling (amino acid and HOBt 2 eq) 5 min.
8. coupling (DCC 2 eq) 60 min.

After step 5, the collected wash solution is, in each case, used for the determination of the loading.

The coupling success is tested qualitatively via the ninhydrin test (Kaiser test) after removal of a small amount of resin—E. Kaiser et al, Anal. Biochem. 34, 595(1970)7. A possible coupling repetition was not necessary in the case of the synthesis carried out.

Splitting off of the protective groups and splitting off from the resin

At the end of the synthesis, the batch was divided into 3 parts and these worked up separately.

a) hPTH(1-35), (acid: PTH(1-35)-Z with Z=COOH)

The splitting off of the protective groups and the splitting off from the resin took place in one step by means of trifluoroacetic acid/phenol/water/thioanisole/ethanediol (16.6:1:1:1:0.5).

b) bPTH(1-35)-amide, (PTH(1-35)-Z with Z=$CONH_2$)

This was obtained by treatment of the peptide resin with $NH_3$ in DMF (1:1) and subsequent splitting off of protective groups as above.

c) hPTH(1-35)-ethylamide (PTH(1-35)-Z with Z=CONH $C_{2-5}$)

This was obtained by treatment of the peptide resin with 70% aqueous ethylamine and subsequent splitting off of protective groups as above.

After evaporation in a vacuum, in each case precipitation was performed with absolute ether. The crude peptides showed, in the case of HPLC analysis, a content of end product of 35% (acid and ethylamide) or of 30% (amide) (area percent).

Analysis of the fragments a)–c):

HPLC system: gradient of A (water, 0.1 of TFA) and B (water 35/acetonitrile 65, 0.1% of TFA). Start with 100%, A linear in 40 min to 100% B. Column Hypersil ODS 5 µ250×4.6 mm.

The preparative purification took place under analogous conditions by means of preparative HPLC (Nova-Prep, Merck).

One obtained 2.7 g hPTH(1-35) acid, 2.6 g hPTH(1-35)-ethylamide and 2.1 g hPTH(1-35)-amide. Purity according to HPLC >95%.

---

We claim:

1. A peptide fragment of a parathyroid hormone (PTH) selected from the group consisting of bovine PTH beginning at residue 1 and ending a residue 35 or 36; and porcine PTH beginning at residue 1 and ending at residue 35 or 36.

2. A process for the preparation of a peptide of claim 1, comprising:

synthesizing fragments by solid phase and liquid phase synthesis from protected amino acids;

splitting off the fragments and the protecting groups; and precipitating the synthesized fragments.

3. The process of claim 2, wherein the synthesized PTH fragments are purified by chromatography processes.

4. A pharmaceutical composition comprising a peptide of claim 1 and a pharmaceutically acceptable excipient.

5. The pharmaceutical composition of claim 4, wherein the peptide is in amounts of from 300 microgram to 30 milligram per therapy unit.

6. The pharmaceutical composition of claim 4 wherein the composition has the property of calcium-regulation.

7. The pharmaceutical composition of claim 4 wherein the composition has the property of promoting the incorporation of calcium into the bones.

8. A method of regulating calcium levels in the body comprising administering to a patient in need of such regulating an effective amount of the peptide of claim 1.

9. A method of increasing incorporation of calcium into the bones comprising administering to a patient in need of such treatment an effective amount of the peptide of claim 1.

10. A method of treatment of osteoporosis comprising administering to a patient in need of such treatment an effective amount of the peptide of claim 1.

* * * * *